US010881296B2

(12) United States Patent
Kubo et al.

(10) Patent No.: US 10,881,296 B2
(45) Date of Patent: Jan. 5, 2021

(54) MEASURING DEVICE AND TRANSMISSION METHOD

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 0 days.

(21) Appl. No.: 16/690,221

(22) Filed: Nov. 21, 2019

(65) Prior Publication Data

US 2020/0085302 A1 Mar. 19, 2020

Related U.S. Application Data

(63) Continuation of application No. PCT/JP2018/028811, filed on Aug. 1, 2018.

(30) Foreign Application Priority Data

Aug. 9, 2017 (JP) ................................. 2017-154753

(51) Int. Cl.
*A61B 5/00* (2006.01)
*A61B 5/0205* (2006.01)
(Continued)

(52) U.S. Cl.
CPC .......... *A61B 5/0022* (2013.01); *A61B 5/0205* (2013.01); *A61B 5/0235* (2013.01);
(Continued)

(58) Field of Classification Search
CPC ... A61B 5/0022; A61B 5/0205; A61B 5/0235; A61B 5/1118; H04Q 9/00; H04Q 9/02;
(Continued)

(56) References Cited

U.S. PATENT DOCUMENTS 9,589,462 B1 * 3/2017 Amir ...................... G08C 19/24
9,857,268 B2 * 1/2018 Kondo .................... G01M 7/00
(Continued)

FOREIGN PATENT DOCUMENTS

JP 5852620 B2 2/2016
JP 2017-041770 A 2/2017
(Continued)

OTHER PUBLICATIONS

Official Communication issued in International Patent Application No. PCT/JP2018/028811, dated Aug. 28, 2018.
(Continued)

*Primary Examiner* — Franklin D Balseca
(74) *Attorney, Agent, or Firm* — Keating and Bennett, LLP

(57) ABSTRACT

A measuring device according to one aspect of the present invention includes a processor configured to acquire, from a sensor, a first, a second, a third and a fourth measurement result obtained by measuring a value related to information at time intervals using the sensor, transmit the first measurement and the second measurement result in a one-way communication packet during a first period from when the second measurement result is obtained until the third measurement result is obtained, and transmit the second and the third measurement result in the one-way communication packet during a second period from when the third measurement result is obtained until the fourth measurement result is obtained.

6 Claims, 8 Drawing Sheets

(51) Int. Cl.
*A61B 5/0235* (2006.01)
*A61B 5/11* (2006.01)
*H04Q 9/02* (2006.01)
*H04Q 9/00* (2006.01)

(52) U.S. Cl.
CPC .............. *A61B 5/1118* (2013.01); *H04Q 9/02* (2013.01); *H04Q 9/00* (2013.01); *H04Q 2209/00* (2013.01); *H04Q 2209/40* (2013.01); *H04Q 2209/43* (2013.01); *H04Q 2209/80* (2013.01); *H04Q 2209/826* (2013.01)

(58) Field of Classification Search
CPC ........... H04Q 2209/00; H04Q 2209/40; H04Q 2209/43; H04Q 2209/60; H04Q 2209/80; H04Q 2209/82; H04Q 2209/826; H04Q 2209/84
See application file for complete search history.

(56) References Cited

U.S. PATENT DOCUMENTS

| | | | |
|---|---|---|---|
| 2008/0015422 A1* | 1/2008 | Wessel | G06F 19/3456 600/301 |
| 2016/0029149 A1 | 1/2016 | Morikawa et al. | |
| 2017/0006359 A1 | 1/2017 | Nabetani et al. | |
| 2019/0038217 A1* | 2/2019 | Cho | A61B 5/746 |

FOREIGN PATENT DOCUMENTS

| | | |
|---|---|---|
| WO | 2013/175741 A1 | 11/2013 |
| WO | 2015/190535 A1 | 12/2015 |

OTHER PUBLICATIONS

English translation of Official Communication issued in International Patent Application No. PCT/JP2018/028811, dated Feb. 20, 2020.

* cited by examiner

| Measurement ID | Measurement time | SBP | DBP |
| --- | --- | --- | --- |
| ⋮ | ⋮ | ⋮ | ⋮ |
| 250 | 2017/6/18 22:49 | 122 | 71 |
| 251 | 2017/6/19 7:21 | 114 | 79 |
| 252 | 2017/6/19 23:03 | 119 | 80 |
| 253 | 2017/6/20 7:16 | 117 | 79 |
| 254 | 2017/6/20 13:28 | 135 | 89 |
| 255 | 2017/6/20 23:05 | 124 | 84 |
| 256 | 2017/6/21 7:18 | 116 | 80 |
| 257 | 2017/6/21 22:58 | 121 | 81 |

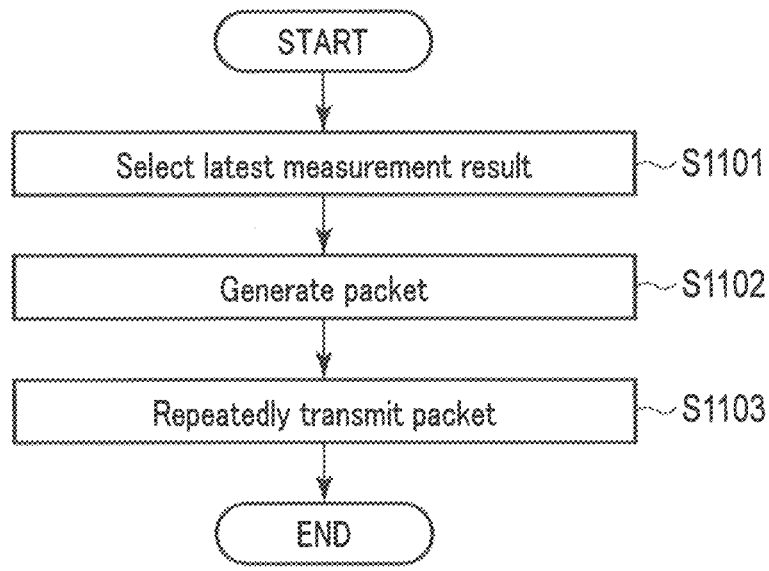
F I G. 11
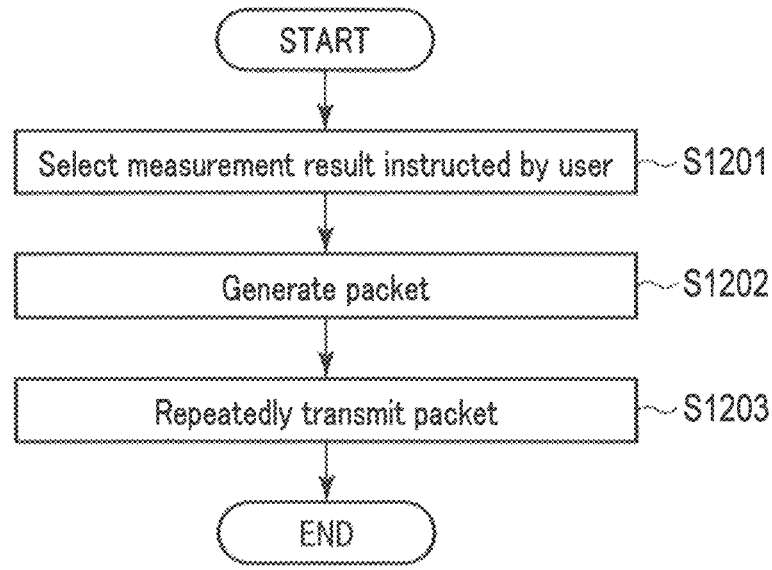
F I G. 12

MEASURING DEVICE AND TRANSMISSION METHOD

CROSS-REFERENCE TO RELATED APPLICATIONS

This application is a Continuation application of PCT Application No. PCT/JP2018/028811, filed Aug. 1, 2018 and based upon and claiming the benefit of priority from Japanese Patent Application No. 2017-154753, filed Aug. 9, 2017, the entire contents of all of which are incorporated herein by reference.

FIELD

The present invention relates to a technique in which a quantity related to information such as biological information is measured using a sensor and a measurement result thus obtained is transmitted by one-way communication.

BACKGROUND

Blood pressure monitors having a function of transferring blood pressure data to a user's mobile terminal have been put on the market. Those blood pressure monitors enable a user to browse his or her blood pressure measurement result on his or her mobile terminal. Typically, a short-range communication technique such as Bluetooth (registered trademark) is used to transmit blood pressure data. Bluetooth communication generally consumes less power than WLAN (Wireless Local Area Network) communication. Bluetooth version 4.0 is also called Bluetooth Low Energy (BLE) and achieves a further reduction of consumed power as compared to previous versions.

BLE supports two-way communication called connection. However, the connection has a problem that operations imposed on a user for pairing are complicated. Furthermore, the connection involves complicated communication procedures, thereby leading to such problems that compatibility problems often occur between a blood pressure monitor and a mobile terminal, each of the blood pressure monitor and the mobile terminal requires high-performance hardware (processor or memory), development/evaluation costs are high, communications start slowly, and so on.

On the other hand, BLE also supports one-way communication called advertising. Japanese Patent No. 5,852,620 discloses a technique in which optional data is included and transmitted in a data field margin portion of an advertisement packet for detecting a wireless communication device as a connection partner.

When blood pressure data is transmitted in one-way communication, pairing and subsequent complicated communication procedures are no longer required. Thus, the problems described above can be solved or reduced. However, a blood pressure monitor with only a transmission function cannot keep track of a state of a mobile terminal (data reception status, etc.). Therefore, such a blood pressure monitor cannot detect the occurrence of data loss in a mobile terminal.

SUMMARY

A measuring device according to one aspect of the present invention includes a measurement result acquisition unit configured to acquire, from a sensor, a plurality of measurement results obtained by measuring a value related to information at time intervals using the sensor, the plurality of measurement results including a first measurement result, a second measurement result obtained after the first measurement result, a third measurement result obtained after the second measurement result, and a fourth measurement result obtained after the third measurement result, and a transmission processing unit configured to transmit a plurality of measurement results including the first measurement result and the second measurement result, in a one-way communication packet during a first period from when the second measurement result is obtained until the third measurement result is obtained, and to transmit a plurality of measurement results including the second measurement result and the third measurement result, in the one-way communication packet during a second period from when the third measurement result is obtained until the fourth measurement result is obtained.

According to the above configuration, the second measurement result is transmitted during not only the first period from when the second measurement result is obtained until the third measurement result is obtained, but also the second period from when the third measurement result is obtained until the fourth measurement result is obtained. Accordingly, the second measurement result can be received by the receiving side during the second period even if it is not received by the receiving side during the first period. This increases the possibility that the receiving side successfully receives the second measurement result. As a result, the occurrence of data loss can be reduced on the receiving side.

The measuring device according to the aspect may further include a transmission ratio determination unit configured to determine a transmission ratio indicating a number of packets used to transmit each measurement result with respect to a number of packets transmitted in one cycle. In this case, the transmission ratio determination unit sets during the second period, a transmission ratio for the second measurement result to a value smaller than a value of a transmission ratio for the third measurement result.

According to the above configuration, the third measurement result with a low possibility of being successfully received by the receiving side can be transmitted at a high density, and the second measurement result with a high possibility of being successfully received by the receiving side can be transmitted at a low density. As a result, the occurrence of data loss can be reduced on the receiving side while facilitating the receiving side's reception of a newly obtained measurement result.

The measuring device according to the aspect may further include an instruction acquisition unit configured to acquire from a user, an instruction for designating a fifth measurement result selected by the user from the acquired measurement results, and a display control unit configured to display the fifth measurement result on a display unit. In this case, the transmission processing unit transmits only the fifth measurement result in the one-way communication packet during a third period in which the fifth measurement result is displayed on the display unit.

According to the above configuration, a measurement result designated by a user is transmitted. This enables the measuring device to transmit a measurement result that has not been received by the receiving side. As a result, data loss on the receiving side can be resolved.

In the measuring device according to the aspect, the transmission processing unit may transmit only the second measurement result in the one-way communication packet until a predetermined time elapses after the second measurement result is obtained.

According to the above configuration, only the latest measurement result is transmitted immediately after the measurement. This increases the possibility that the latest measurement result is successfully received by the receiving side, and enables a user to browse the latest measurement result using a device on the receiving side device immediately after the measurement.

In the measuring device according to the aspect, the information includes at least one of user's biological information and user's activity information. This configuration enables a device on the receiving side to manage biological information such as blood pressure, or activity information such as the number of steps.

The present invention can provide a measuring device and a transmission method by which the occurrence of data loss can be reduced on a receiving side when a measurement result obtained by measuring a quantity related to information is transmitted by one-way communication.

BRIEF DESCRIPTION OF THE DRAWINGS

FIG. 11 is a flowchart illustrating an example of a transmission operation in a latest measurement result transmission mode according to the present embodiment.

FIG. 12 is a flowchart illustrating an example of a designated measurement result transmission mode according to the present embodiment.

DETAILED DESCRIPTION

Hereinafter, embodiments of the present invention will be described with reference to the drawings.

The object of some embodiments of the present invention is to provide a measuring device and a transmission method by which the occurrence of data loss can be reduced on a receiving side when a measurement result is transmitted by one-way communication.

§ 1 Application Example

Figure 1:
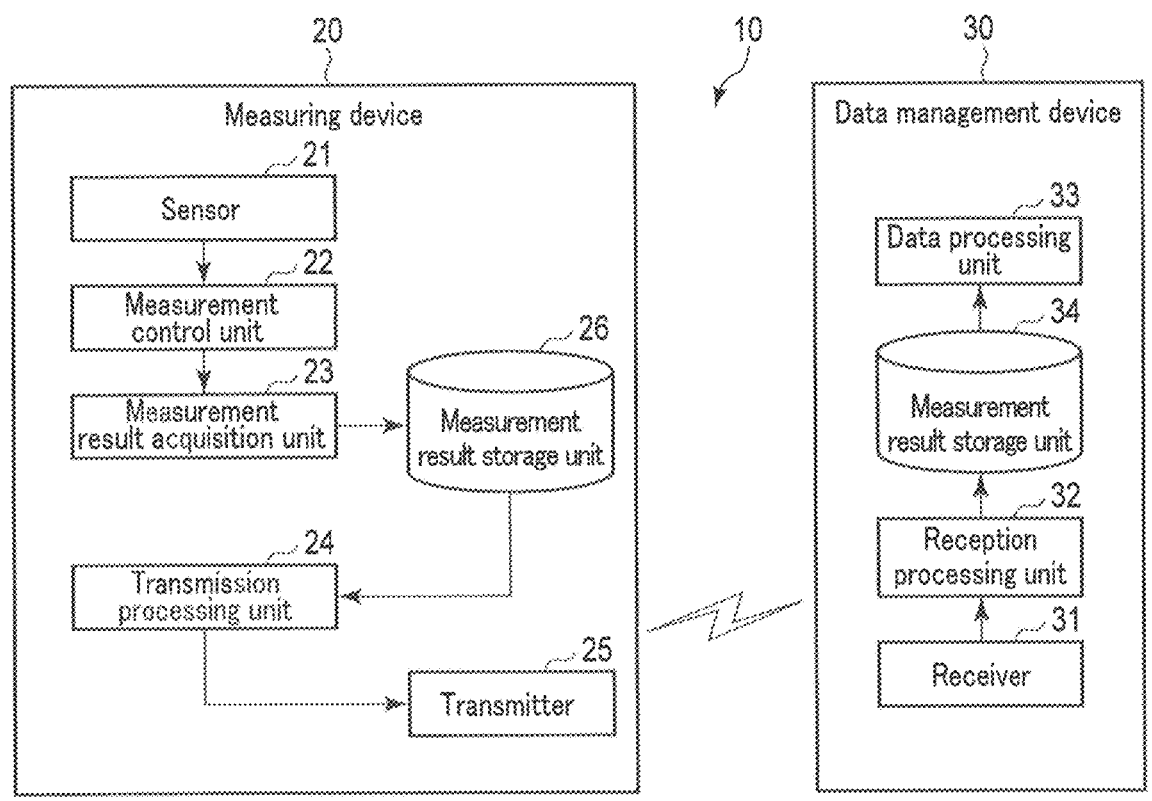
FIG. 1 is a block diagram illustrating a configuration example of a data management system according to an embodiment of the present invention.

An application example of the present invention will be described with reference to FIG. 1. FIG. 1 illustrates a data management system 10 according to an embodiment. As shown in FIG. 1, the data management system 10 includes a measuring device 20 and a data management device 30. In this application example, the measuring device 20 is, for example, a wearable device worn by a user, while the data management device 30 is, for example, a mobile terminal owned by the user. The mobile terminal may be, for example, a smartphone, a mobile phone, a tablet PC (Personal Computer), a notebook PC, etc.

The measuring device 20 includes a sensor 21 and measures a quantity related to information on the user (hereinafter referred to as user information) using the sensor 21. User information includes, for example, at least one of user's biological information and user's activity information. Biological information means information obtained from the user's body. Examples of a quantity related to biological information include blood pressure, a pulse rate, a heart rate, an electrocardiogram, a body temperature, an arterial oxygen saturation, a blood alcohol concentration, a body weight, a body fat percentage, etc. Activity information means information indicating a user's physical activity. Examples of a quantity related to activity information (also called activity quantity) include the number of steps, the number of stair-climbing steps, calorie consumption, etc.

Various types of the sensor 21 are used depending on the type of information on a user to be measured. When a blood pressure value is measured, a pressure sensor, a photoelectric sensor, an ultrasonic sensor, an electrode, or the like is used as the sensor 21. When the number of steps is measured, an acceleration sensor or the like is used as the sensor 21. To simplify explanations, described in the present embodiment is a case in which the measuring device 20 measures a quantity related to one type of user information (for example, blood pressure). However, it should be noted that the measuring device 20 may measure a quantity related to multiple types of user information (for example, a combination of the blood pressure and the number of steps).

The measuring device 20 further includes a measurement control unit 22, a measurement result acquisition unit 23, a transmission processing unit 24, a transmitter 25, and a measurement result storage unit 26. The measurement control unit 22 measures a quantity related to user information using the sensor 21, and generates a measurement result indicating the measured quantity related to user information. The measurement result acquisition unit 23 receives the measurement result from the measurement control unit 22 and stores it in the measurement result storage unit 26. The measurement control unit 22 performs the measurement at time intervals, and the measurement result acquisition unit 23 sequentially obtains measurement results from the measurement control unit 22. A measurement result is typically associated with measurement time information indicating a measurement time.

The transmission processing unit 24 performs processing for transmitting a measurement result. The transmission processing unit 24 selects a plurality of measurement results to be transmitted, from measurement results generated by the measurement control unit 22 and stored in the measurement result storage unit 26. In one example, the transmission processing unit 24 selects a predetermined number of measurement results in order from the latest measurement result. In another example, the transmission processing unit 24 selects measurement results obtained during a predetermined time period (for example, measurement results acquired during the most recent week). Selection processing is not limited to these examples. The transmission processing unit 24 may perform selection processing every time a new measurement result is obtained, or periodically.

The transmission processing unit 24 generates one or more one-way communication packets based on the selected measurement results. Each packet includes at least one of the selected measurement results. For example, the transmission processing unit 24 generates packets respectively including selected measurement results. The transmission processing unit 24 transmits the generated packets. Specifically, the transmission processing unit 24 supplies packets to the transmitter 25, and the transmitter 25 wirelessly transmits the packets in the order of receiving them from the transmission processing unit 24. The transmitter 25 is a transmitter configured to periodically transmit wireless signals to surrounding areas, which is sometimes called a beacon terminal. The transmitter 25 may comply with a short-range wireless communication standard such as Bluetooth or Bluetooth Low Energy (BLE).

Transmission processing of the transmission processing unit 24 will be described with a specific example. Herein, it is assumed that measurement result 1, measurement result 2, and measurement result 3 are obtained in this order, and those three measurement results are transmitted during a period from when measurement result 3 is obtained until measurement result 4 is obtained. The transmission processing unit 24 generates three packets, i.e., packet 1 including measurement result 1, packet 2 including measurement result 2, and packet 3 including measurement result 3. The transmission processing unit 24 repeats the operation of transmitting packet 1, packet 2, and packet 3 in this order. That is, the transmission processing unit 24 sequentially transmits packet 1, packet 2, and packet 3 in a manner to transmit packet 1, packet 2, packet 3, packet 1, packet 2, packet 3, packet 1, . . . . In this way, the measuring device 20 repeatedly transmits the measurement results.

A packet may include a plurality of measurement results. In the case of including two measurement results in each packet, the transmission processing unit 24 may generate two packets, for example, packet 1 including measurement result 1 and measurement result 2, and packet 2 including measurement result 1 and measurement result 3. In another example, the transmission processing unit 24 may generate three packets, i.e., packet 1 including measurement result 1 and measurement result 2, packet 2 including measurement result 1 and measurement result 3, and packet 3 including measurement result 2 and measurement result 3. The transmission processing unit 24 may generate one packet including measurement result 1, measurement result 2, and measurement result 3, and repeatedly transmit this packet.

The data management device 30 manages measurement results obtained by the measuring device 20, and includes a receiver 31, a reception processing unit 32, a data processing unit 33, and a measurement result storage unit 34.

The data management device 30 typically includes a transceiver in compliance with a wireless communication standard that is identical to or compatible with that of the transmitter 25 of the measuring device 20, and the receiver 31 is a part of this transceiver. The receiver 31 receives a packet from the measuring device 20 and provides the received packet to the reception processing unit 32. The reception processing unit 32 extracts a measurement result from the packet and stores it in the measurement result storage unit 34. Since the measuring device 20 transmits the same measurement result many times, the reception processing unit 32 may acquire the same measurement result as that already acquired. In this case, the reception processing unit 32 discards a duplicated measurement result thus obtained, without storing it in the measurement result storage unit 34. The data processing unit 33 processes measurement results stored in the measurement result storage unit 34. For example, the data processing unit 33 presents measurement results to a user by performing statistical processing or graphing.

The data management system 10 may have a situation in which the data management device 30 fails to receive a packet from the measuring device 20. This situation occurs because, for example, the data management device 30 is away from the measuring device 20, the data management device 30 is turned off, the wireless communication function of the data management device 30 is turned off, and so on. Assume that the measuring device 20 transmits only a measurement result obtained by the first measurement during a period between the first measurement and the second measurement (in this case, only a measurement result obtained by the second measurement is transmitted during a period between the second measurement and the next third measurement). In this case, unless the data management device 30 receives this particular measurement result from the measuring device 20 during this particular period, the data management device 30 would lose an opportunity to receive this measurement result. In some cases, some degree of data loss may be allowed to occur on the data management device 30; however, in many cases, it is preferable that the data management device 30 receives all measurement results obtained by the measuring device 20.

In the present embodiment, the measuring device 20 is configured to transmit a plurality of measurement results including the second measurement result and the first measurement result obtained before the second measurement result in a one-way communication packet during the first period from when the second measurement result is obtained until the next third measurement result is obtained, and to transmit a plurality of measurement results including the second measurement result and the third measurement result in a one-way communication packet during the second period from when the third measurement result is obtained until the next fourth measurement result is obtained. That is, the second measurement result is transmitted during not only the first period but also the second period. Accordingly, the second measurement result can be received by the data management device 30 during the second period even if it is not received by the data management device 30 during the first period. This means that each of measurement results is transmitted over a longer period of time and has a higher probability of being successfully received by the data management device 30 as compared to a case in which only the latest measurement result is transmitted (in this case, only the second measurement result is transmitted during the first period, and only the third measurement is transmitted during the second period). As a result, the occurrence of data loss can be reduced in the data management device 30.

Next, the measuring device 20 and the data management device 30 will be described in more detail. In the example described below, the measuring device 20 is a blood pressure monitor of a wristwatch type, and measures a blood pressure on a wrist as a site to be measured. Note that a site to be measured is not limited to the wrist, but may be another site such as the upper arm.

Figure 2:
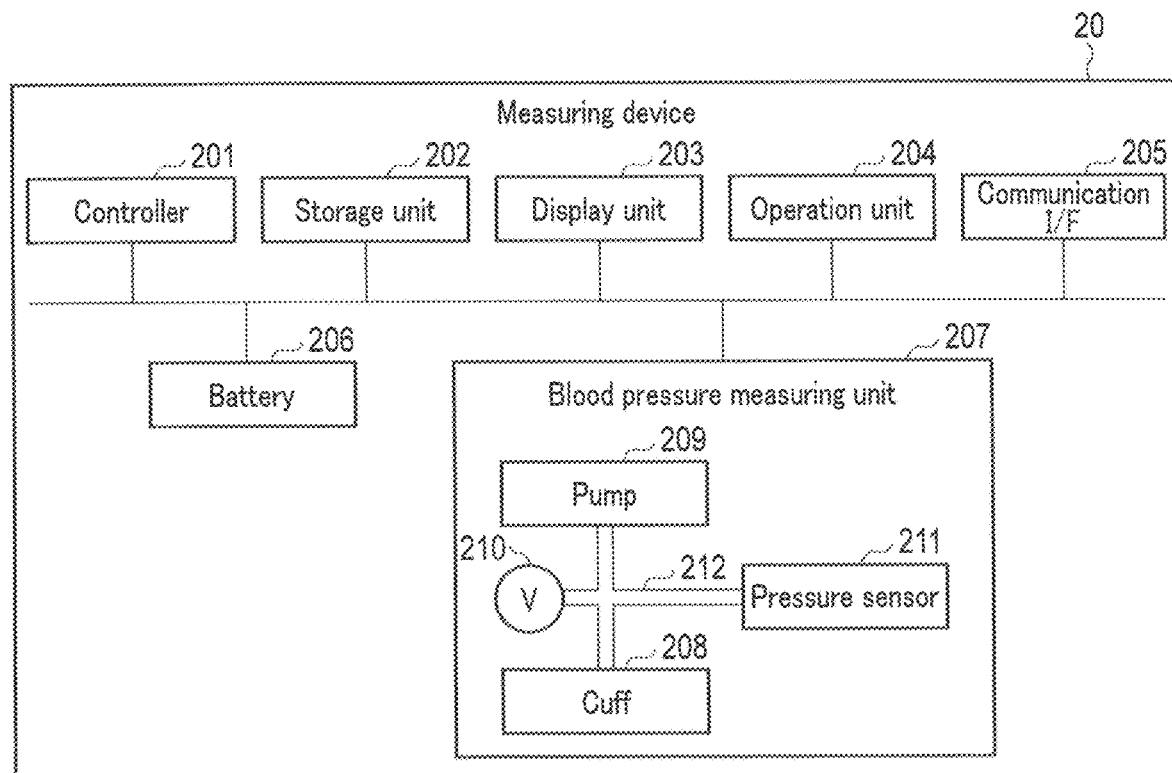
FIG. 2 is a block diagram illustrating an example of a hardware configuration of a measuring device illustrated in FIG. 1.

§ 2 Structural Example (Hardware Structure)
<Measuring Device>
FIG. 2 illustrates an example of a hardware configuration of the measuring device 20. As illustrated in FIG. 2, the measuring device 20 includes a controller 201, a storage unit 202, a display unit 203, an operation unit 204, a communication interface 205, a battery 206, and a blood pressure measuring unit 207.

The controller 201 includes a central processing unit (CPU), a random access memory (RAM), a read only memory (ROM), etc., and controls each element according to data processing. The storage unit 202 is an auxiliary storage device such as a semiconductor memory (for example, a flash memory). The storage unit 202 stores a blood pressure measurement program to be executed by the controller 201, measurement result data indicating a blood pressure value calculated by the controller 201, etc. The blood pressure measurement program is a program for causing the measuring device 20 to measure a user's blood pressure.

The display unit 203 displays information such as a measurement result. As the display unit 203, for example, a liquid crystal display (LCD), an organic light emitting diode (OLED) display, etc., may be used. The operation unit 204 allows a user to input an instruction directed to the measuring device 20. The operation unit 204 provides the controller 201 with an instruction signal in accordance with an operation by a user. The operation unit 204 includes, for example, a plurality of push buttons. As a combination of the display unit 203 and the operation unit 204, a touch screen may be used.

In the present embodiment, the operation unit 204 includes the first to third buttons. The first button is used to switch screens. The second button is used to indicate a determination. The third button is used to indicate cursor movement. For example, when the first button is pressed by a user while a home screen is displayed on the display unit 203, the display unit 203 is caused to display a screen for confirming whether or not to perform blood pressure measurement. When the second button is pressed while the confirmation screen is displayed, the measuring device 20 performs blood pressure measurement. Furthermore, when the first button is pressed while the confirmation screen is displayed, the display unit 203 is caused to display a screen for browsing a measurement result history. The history browsing screen includes, for example, a list of measurement results (for example, a list of measurement IDs or measurement times). A user moves a cursor to a desired measurement result using the third button, and presses the second button. This causes the display unit 203 to display details of the desired measurement result. When the first button is pressed while the history browsing screen is displayed, the display unit 203 is caused to display the home screen.

Figures 5, 6:
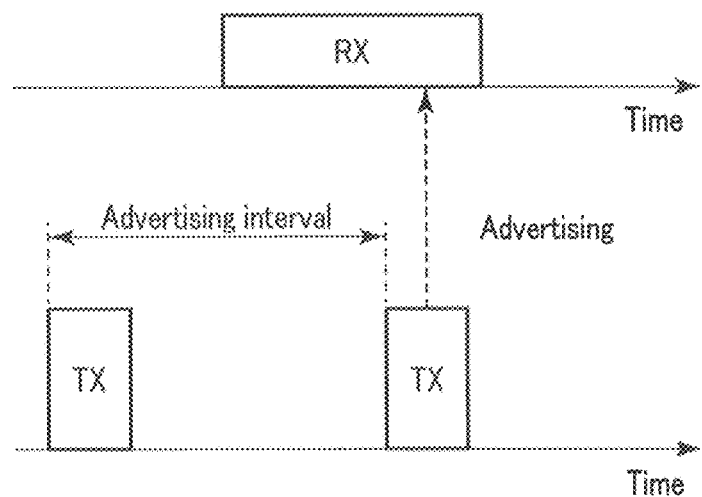
FIG. 5 is a diagram illustrating a part of data stored in a measurement result storage unit illustrated in FIG. 4.
FIG. 6 is a diagram for explaining advertising performed in BLE.

The communication interface 205 is an interface for communicating with an external device. In this embodiment, the communication interface 205 includes only a transmitter that periodically broadcasts radio signals. That is, the communication interface 205 has a transmission function but no reception function. The transmitter performs transmission processing including up-conversion and amplification. A transmitter that consumes low power is desirable. In the present embodiment, the communication interface 205 complies with BLE, and uses a communication method called advertising that broadcasts signals without connecting to any network. An interval between the transmissions described above corresponds to a so-called advertising interval in BLE. As shown in FIG. 6, an advertising interval corresponds to a time interval between one advertising communication and another advertising communication. The advertising interval can be set in units of 0.625 [ms] in the range of 20 [ms] to 10.24 [s]. For advertising communication, three channels called advertising channels are used. In one advertising communication, signals are transmitted using the three channels sequentially.

In another embodiment, the communication interface 205 may further include a communication module that enables bidirectional communication. The communication module may be a wireless communication module or a wired communication module, or may include both of them.

The battery 206 is a rechargeable secondary battery, for example. The battery 206 supplies power to each element in the measuring device 20. The battery 206 supplies power to the controller 201, the storage unit 202, the display unit 203, the operation unit 204, the communication interface 205, and the blood pressure measuring unit 207, for example.

The blood pressure measuring unit 207 measures a user's blood pressure. In the example shown in FIG. 2, the blood pressure measuring unit 207 includes a cuff 208, a pump 209, an exhaust valve 210, and a pressure sensor 211. The cuff 208 includes an air bag. The air bag is connected to the pump 209 and the exhaust valve 210 via an air passage 212. The pump 209 supplies air to the air bag of the cuff 208. When air is supplied to the air bag by the pump 209, the air bag is inflated. The inflation of the air bag causes the cuff 208 to press a site to be measured (in this example, a wrist). The exhaust valve 210 is provided to exhaust air from the air bag of the cuff 208. Driving of the pump 209 and both opening and closing of the exhaust valve 210 are controlled by the controller 201. The pressure sensor 211 detects pressure inside the cuff 208 and outputs a pressure signal indicating the detected pressure to the controller 201. The controller 201 calculates a blood pressure value based on the pressure signal received from the pressure sensor 211. Blood pressure values include, but are not limited to, systolic blood pressure (SBP) and diastolic blood pressure (DBP).

Although not shown in FIG. 2, an amplifier configured to amplify an output signal of the pressure sensor 211, and an analog-to-digital converter configured to convert an output signal of the amplifier from an analog signal to a digital signal, are provided between the pressure sensor 211 and the controller 201.

Regarding a specific hardware configuration of the measuring device 20, elements can be omitted, replaced, and added as appropriate according to the embodiment. For example, the controller 201 may include a plurality of processors.

Figure 3:
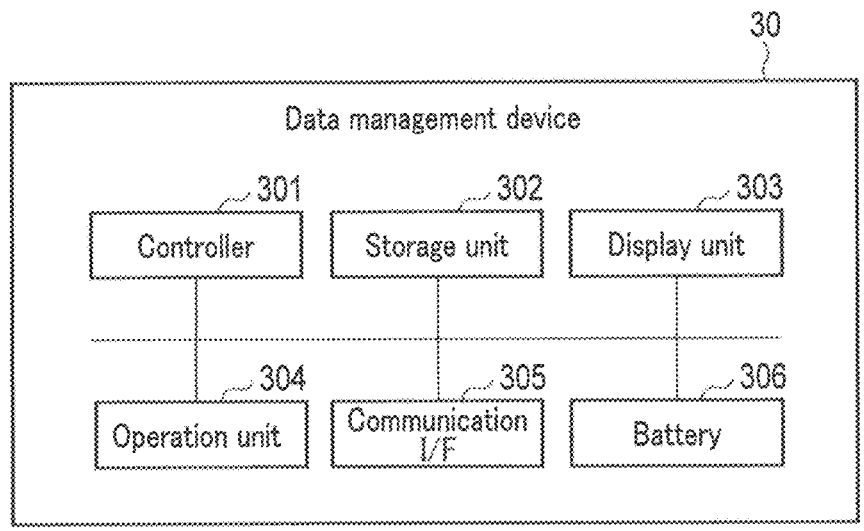
FIG. 3 is a block diagram illustrating an example of a hardware configuration of a data management device illustrated in FIG. 1.

<Data Management Device>
FIG. 3 illustrates an example of a hardware configuration of the data management device 30. As illustrated in FIG. 3, the data management device 30 includes a controller 301, a storage unit 302, a display unit 303, an operation unit 304, a communication interface 305, and a battery 306.

The controller 301 includes a CPU, a RAM, a ROM, etc., and controls each element in accordance with data processing. The storage unit 302 is an auxiliary storage device such as a hard disk drive (HDD), a semiconductor memory (for example, a solid state drive (SSD)), etc. The storage unit 302 stores a data management program to be executed by the controller 301, data on measurement results received from the measuring device 20, etc. The data management program is a program for causing the measuring device 20 to manage measurement results.

The combination of the display unit 303 and the operation unit 304 is realized by a touch screen. The touch screen may be of a pressure-sensitive (resistive) type or a proximity (capacitance) type. As the display unit 303, for example, an LCD, an OLED display, etc., can be used. The operation unit 204 enables a user to input an instruction directed to the data management device 30. The operation unit 304 provides the controller 301 with an instruction signal corresponding to an operation by a user. The operation unit 304 may further include a plurality of push buttons. The display unit 303 and the operation unit 304 may be realized as separate devices.

The communication interface 305 is an interface for communicating with an external device. In order to receive packets from the measuring device 20, the communication interface 305 includes a wireless communication module corresponding to a wireless communication standard that is identical to or compatible with that of the communication interface 205 of the measuring device 20. This wireless communication module performs reception processing including amplification and down-conversion on a received signal. In the present embodiment, the communication interface 305 includes a BLE communication module. This BLE communication module is also usable for bidirectional communication with an external device independent of the measuring device 20. The communication interface 305 may further include an additional wireless communication module. For example, the communication interface 305 includes a Wi-Fi (registered trademark) module, is connected to a network (for example, the Internet) via a Wi-Fi base station, and communicates with an external device via the network. The communication interface 305 may further include a wired communication module. For example, the communication interface 305 may include a USB connector and connect to an external device via a USB cable.

The battery 306 is a rechargeable secondary battery, for example. The battery 306 supplies power to each element within the data management device 30. The battery 306 supplies power to the controller 301, the storage unit 302, the display unit 303, the operation unit 304, and the communication interface 305, for example.

Regarding a specific hardware configuration of the data management device 30, elements can be omitted, replaced, and added as appropriate according to the embodiment. For example, the controller 301 may include a plurality of processors. Furthermore, the data management device 30 may be realized by a plurality of information processing devices (computers).

(Software Configuration)
<Measuring Device>

Figure 4:
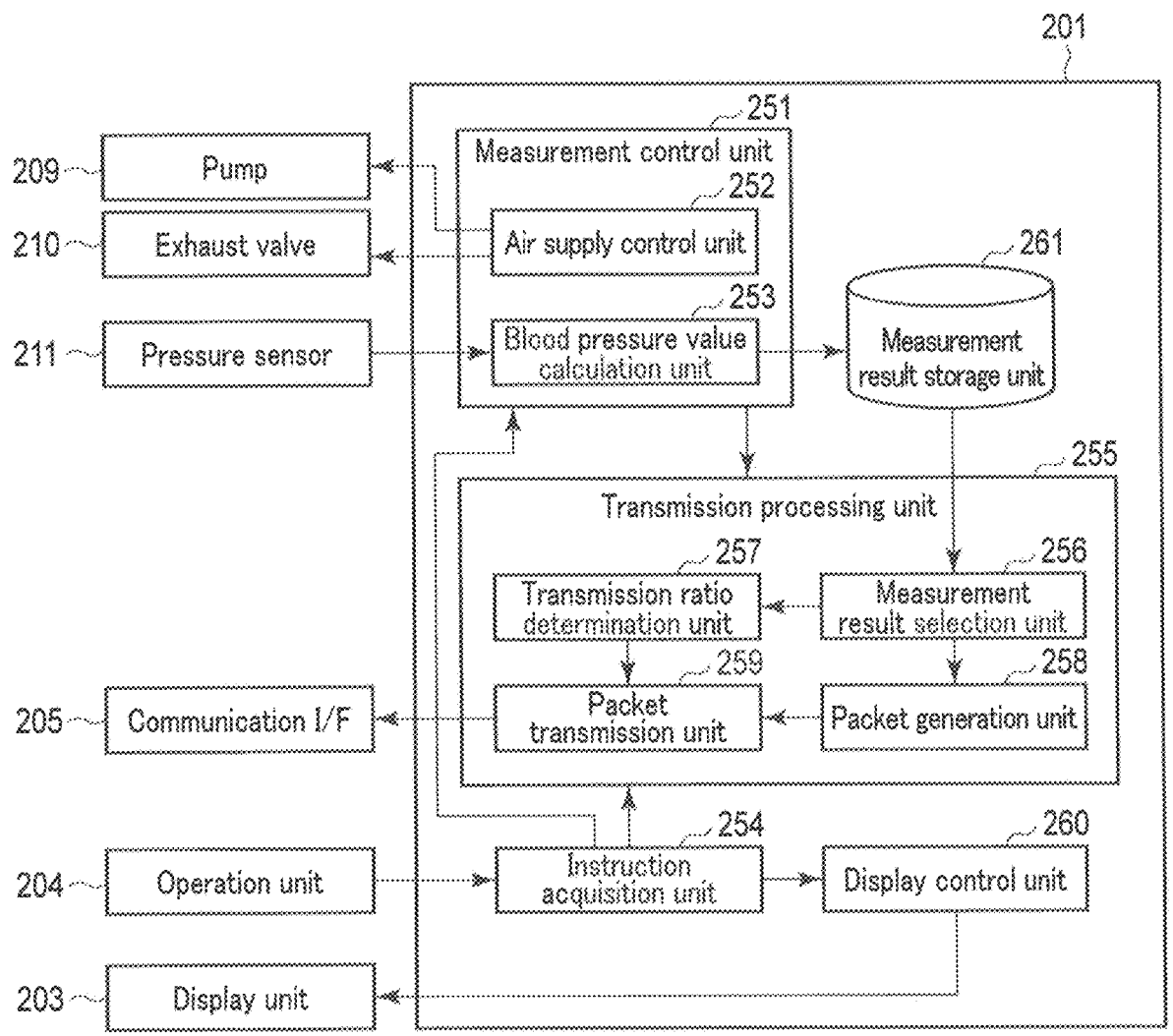
FIG. 4 is a block diagram illustrating an example of a software configuration of the measuring device illustrated in FIG. 1.

With reference to FIG. 4, an example of a software configuration of the measuring device 20 will be described.

The controller 201 of the measuring device 20 (FIG. 2) loads into the RAM, a blood pressure measurement program stored in the storage unit 202. Then, the controller 201 causes the CPU to interpret and execute the blood pressure measurement program loaded into the RAM, thereby controlling each element. In this manner, as illustrated in FIG. 4, the measuring device 20 functions as a computer including a measurement control unit 251, an instruction acquisition unit 254, a transmission processing unit 255, a display control unit 260, and a measurement result storage unit 261. The measurement result storage unit 261 is realized by the storage unit 202.

The measurement control unit 251 measures a user's blood pressure. In one example, the measurement control unit 251 starts measurement when a recommended condition for measuring blood pressure is satisfied. Such conditions include, for example, a condition that a present time reaches a preset time (for example, 7:30 a.m. and 10:30 p.m.). In another example, the measurement control unit 251 starts measurement in response to a user's operation.

The measurement control unit 251 includes an air supply control unit 252 and a blood pressure value calculation unit 253. The air supply control unit 252 controls the supply of fluid to the cuff 208. Specifically, the air supply control unit 252 controls driving of the pump 209 and both opening and closing of the exhaust valve 210. The blood pressure value calculation unit 253 calculates a blood pressure value by an oscillometric method based on a pressure signal received from the pressure sensor 211, in a pressurizing process for supplying air to the cuff 208 or a depressurizing process for exhausting air from the cuff 208. A pulse rate can be calculated simultaneously with a blood pressure value. The blood pressure value calculation unit 253 stores a measurement result indicating the calculated blood pressure value in the measurement result storage unit 261 in a manner such that the measurement result is associated with measurement time information.

The instruction acquisition unit 254 acquires an instruction input by a user using the operation unit 204. Examples of the instruction include an instruction to start measurement, an instruction for browsing measurement result history, etc. Upon acquisition of an instruction to start measurement, the instruction acquisition unit 254 provides this instruction to the measurement control unit 251. Upon acquisition of a history browsing instruction, the instruction acquisition unit 254 provides this instruction to the display control unit 260.

The display control unit 260 controls the operation of the display unit 203. The display control unit 260 changes the display content in response to a user's operation. In addition, immediately after a new measurement result is obtained, the display control unit 260 causes the display unit 203 to display this new measurement result.

The transmission processing unit 255 reads from the measurement result storage unit 261 one or more measurement results to transmit, and generates one or more one-way communication packets based on the read one or more measurement results. The transmission processing unit 255 transmits the generated packets via the communication interface 205.

The transmission processing unit 255 includes a measurement result selection unit 256, a transmission ratio determination unit 257, a packet generation unit 258, and a packet transmission unit 259. The transmission processing unit 255 has a plurality of transmission modes. In the present embodiment, the transmission processing unit 255 has three transmission modes, i.e., a normal transmission mode, a latest measurement result transmission mode, and a designated measurement result transmission mode. The transmission processing unit 255 may have only one transmission mode (for example, the normal transmission mode).

First, a case in which the transmission processing unit 255 operates in the normal transmission mode will be described.

The measurement result selection unit 256 selects a plurality of measurement results to transmit, from measurement results stored in the measurement result storage unit 261. The transmission ratio determination unit 257 determines a transmission ratio for each of the measurement results selected by the measurement result selection unit 256. A transmission ratio means a ratio of the number of packets used to transmit each measurement result to the number of packets transmitted in one cycle. A transmission ratio is expressed in fractions, decimals, integers, etc. The transmission ratio determination unit 257 provides information indicating a determined transmission ratio to the packet transmission unit 259.

The packet generation unit 258 generates one or more packets based on the plurality of measurement results selected by the measurement result selection unit 256, and provides the plurality of generated packets to the packet transmission unit 259. At least one of the measurement results selected by the measurement result selection unit 256 is assigned to each packet. The packet transmission unit 259 transmits a plurality of packets generated by the packet generation unit 258 according to the transmission ratio determined by the transmission ratio determination unit 257.

A specific example of the transmission processing will be described. Assume that the data shown in FIG. 5 is obtained. In FIG. 5, each entry includes data indicating a measurement ID, a measurement time, SBP, and DBP. The measurement ID is a serial number indicating a measurement order. A measurement ID is also simply referred to as ID. Assume that data transmitted during a period from when the measurement result assigned with ID=257 is obtained until the measurement result assigned with ID=258 is obtained is data for the latest three days, that is, measurement results with IDs 251 to 257. The measurement result selection unit 256 selects seven measurement results assigned with IDs 251 to 257, and provides data including these seven measurement results to the transmission ratio determination unit 257 and the packet generation unit 258.

The transmission ratio determination unit 257 determines a transmission ratio for each of these seven measurement results. In the present embodiment, the transmission ratio determination unit 257 sets a higher transmission ratio for a newer measurement result. For example, in the case of transmitting N measurement results, the transmission ratio determination unit 257 sets the transmission ratio of (N−M+1)/ΣN for the M-th latest measurement result. Here, M is an integer ranging from 1 to N. ΣN corresponds to the number of packets transmitted in one cycle, and N−M+1 corresponds to the number of packets used to transmit the M-th latest measurement result. In this example, the transmission ratio determination unit 257 sets the transmission ratio of 7/28 for the measurement result with ID=257, the transmission ratio of 6/28 for the measurement result with ID=256, the transmission ratio of 5/28 for the measurement result with ID=255, the transmission ratio of 4/28 for the measurement result with ID=254, the transmission ratio of 3/28 for the measurement result with ID=253, the transmission ratio of 2/28 for the measurement result with ID=252, and the transmission ratio of 1/28 for the measurement result with ID=251.

The packet generation unit 258 generates seven packets that respectively include the measurement results with ID=251 to ID=257. These packets are denoted as packet 1, packet 2, . . . , and packet 7 in order of acquisition. For example, packet 1 represents a packet including the measurement result with ID=251. The packet transmission unit 259 transmits packet 7, packet 6, . . . , and packet 1 in this order, subsequently transmits packet 7, packet 6, . . . , and packet 2 in this order, and further transmits packet 7, packet 6, packet 5, packet 4, packet 3, packet 7, packet 6, packet 5, packet 4, packet 7, packet 6, packet 5, packet 7, packet 6, and packet 7, in this order. In this transmission operation, packet 7 is transmitted 7 times, packet 6 is transmitted 6 times, packet 5 is transmitted 5 times, packet 4 is transmitted 4 times, packet 3 is transmitted 3 times, packet 2 is transmitted twice, and packet 1 is transmitted once. In this way, each of packets 1 to 7 is transmitted at a transmission ratio determined by a transmission ratio determination unit 257. The packet transmission unit 259 repeats this transmission operation.

The order of transmitting packets 1 to 7 is not limited to the above example as long as they are transmitted according to their transmission ratio determined by the transmission ratio determination unit 257. For example, the packet generation unit 258 may transmit packet 7 seven times continuously, then transmit packet 6 six times continuously . . . , transmit packet 2 twice continuously, and finally transmit packet 1 once.

Alternatively, the packet generation unit 258 may generate a packet set (a set of packets transmitted in one cycle) according to a transmission ratio determined by the transmission ratio determination unit 257. Referring to the above example, the packet generation unit 258 generates a packet set including seven packets 7, six packets 6, . . . , and one packet 1. The packet transmission unit 259 repeats the operation of transmitting this packet set generated by the packet generation unit 258.

In the above example, a chronological order of measurement results is based on a measurement order. A chronological order of measurement results may be based on a date. In this case, the measurement results obtained on the same date are assigned with the same transmission ratio. For example, the transmission ratio determination unit 257 sets the transmission ratio of 3/14 for the measurement results with ID=257 and ID=256, the transmission ratio of 2/14 for the measurement results with ID=255, ID=254, and ID=253, and the transmission ratio of 1/14 for the measurement results with ID=252 and ID=251.

Next, a case in which the transmission processing unit 255 operates in the latest measurement result transmission mode will be described.

The latest measurement result transmission mode is a mode in which the latest measurement result generated by the measurement control unit 251 is intensively transmitted. At the end of blood pressure measurement, a measurement result obtained by this measurement has not been transmitted yet, and thus the data management device 30 has not received this measurement result. The transmission processing unit 255 operates in the latest measurement result transmission mode and intensively transmits the latest measurement result until a predetermined time elapses after the latest measurement result is generated by the measurement control unit 251. This facilitates the data management device 30's reception of the latest measurement result, and allows a user to browse the latest measurement result with the data management device 30 immediately after the measurement.

When the blood pressure measurement is completed, the measurement control unit 251 transmits to the transmission processing unit 255, measurement completion information indicating that the latest measurement result has been obtained. When the transmission processing unit 255 receives the measurement completion information from the measurement control unit 251, the transmission mode is switched from the normal transmission mode to the latest measurement result transmission mode. In the present embodiment, the transmission processing unit 255 operating in the latest measurement result transmission mode transmits only the latest measurement result. In this case, the transmission ratio determination unit 257 may not operate. The measurement result selection unit 256 reads the latest measurement result from the measurement result storage unit 261. The packet generation unit 258 generates a packet including the latest measurement result selected by the measurement result selection unit 256, and the packet transmission unit 259 transmits this packet. When a certain period of time elapses after the completion of blood pressure measurement (or after a mode is switched to the latest measurement result transmission mode), the transmission mode returns to the normal transmission mode.

In another embodiment, the transmission processing unit 255 operating in the latest measurement result transmission mode transmits a plurality of measurement results including the latest measurement result, and determines transmission ratios for the measurement results in a manner such that the latest measurement result is given the highest transmission ratio. At this time, a transmission ratio of the latest measurement result in the latest measurement result transmission mode is set to be a value larger than that of a transmission ratio of the latest measurement result in the normal transmission mode. Referring to the above example, in the normal transmission mode, the measurement result with ID=257 which is the latest measurement result is given the transmission ratio of 7/28. In the latest measurement result transmission mode, a transmission ratio for the measurement result with ID=257 is set to a value larger than 7/28 (for example, 1/2).

Next, a case in which the transmission processing unit 255 operates in the designated measurement result transmission mode will be described.

The designated measurement result transmission mode is a mode in which a measurement result designated by a user is intensively transmitted. When a user is browsing a measurement result history on the measuring device 20, the transmission processing unit 255 operates in the designated measurement result transmission mode. A user inputs an instruction using the operation unit 204, and a measurement result designated by this instruction is displayed on the display unit 203. During a period in which the designated measurement result is displayed on the display unit 203, the transmission processing unit 255 operates in the designated measurement result transmission mode, and intensively transmits the designated measurement result. This makes it easy for the data management device 30 to receive the measurement result designated by a user. For example, measurement data that has not been received by the data management device 30 is specified. As a result, the data loss can be solved in the data management device 30. A user operation for causing the display unit 203 to display thereon a specific measurement result corresponds to an instruction for causing the measuring device 20 to transmit this specific measurement result.

Assume that the data management device 30 has not received the measurement result with ID=255 shown in FIG. 5. When acquiring from a user, an instruction for causing the display unit 203 to display thereon the measurement result with ID=255, the operation unit 204 passes this instruction to the display control unit 260. The display control unit 260 displays the measurement result with ID=255 on the display unit 203 in response to the instruction input from the user. At this time, the display control unit 260 provides the transmission processing unit 255 with identification information for identifying the measurement result displayed on the display unit 203 (in this example, information indicative of ID=255). Accordingly, a transmission mode of the transmission processing unit 255 is switched to the designated measurement result transmission mode.

In the present embodiment, the transmission processing unit 255 operating in the designated measurement result transmission mode transmits only a measurement result designated by a user (that is, a measurement result displayed on the display unit 203). The measurement result selection unit 256 reads the measurement result with ID=255 from the measurement result storage unit 261. The packet generation unit 258 generates a packet including the measurement result with ID=255. The packet transmission unit 259 repeats the operation of transmitting the generated packet.

In another embodiment, the transmission processing unit 255 operating in the designated measurement result transmission mode transmits a plurality of measurement results including a measurement result designated by a user. At this time, the transmission ratio determination unit 257 determines transmission ratios for these measurement results in a manner such that the designated measurement result is given the highest transmission ratio.

Hereinafter, advertisement of BLE will be schematically described.

In a passive scan method employed in BLE, as illustrated in FIG. 6, a new node periodically transmits advertisement packets for advertising its own presence. An advertising interval, which is an interval between transmissions of advertisement packets, can be set in units of 0.625 [ms] within the range of 20 [ms] to 10.24 [s]. This new node can save power consumption by entering a sleep state between one transmission and a next transmission of advertisement packets. In addition, since an advertisement packet receiving side also operates intermittently, the transmission and reception of advertisement packets involve very small power consumption.

Figure 7:
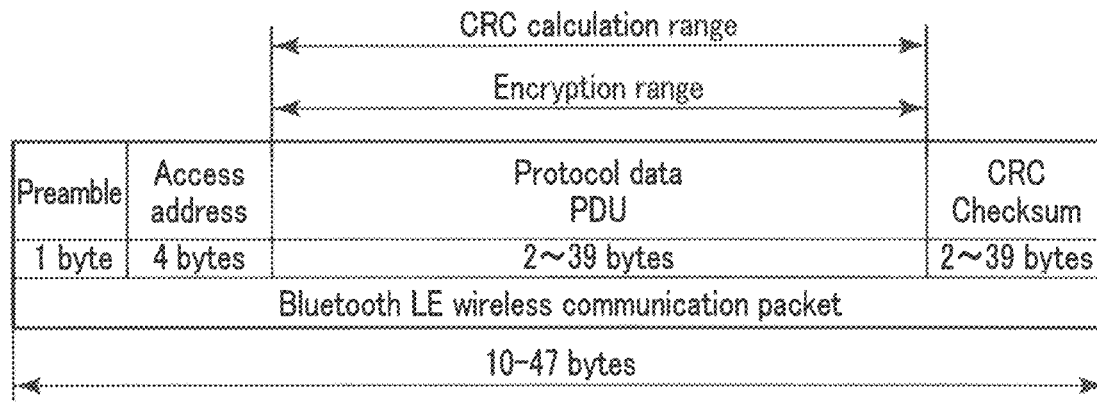
FIG. 7 is a diagram illustrating a data structure of a packet to be transmitted and received in BLE.

FIG. 7 illustrates a basic configuration of a BLE wireless communication packet. A BLE wireless communication packet includes a 1-byte preamble, a 4-byte access address, a 2 to 39-byte (variable) protocol data unit (PDU), and a 3-byte cyclic redundancy checksum (CRC). The length of BLE wireless communication packet depends on the length of the PDU, and is 10 to 47 bytes.

The preamble field is prepared for synchronization of BLE wireless communication and stores the repetition of "01" or "10". The access address stores a fixed numerical value for an advertising channel and a random access address for a data channel. The present embodiment targets an advertisement packet that is a BLE wireless communication packet transmitted on the advertising channel. The CRC field is used for the detection of reception errors. The CRC calculation range includes only the PDU field.

Figure 8:
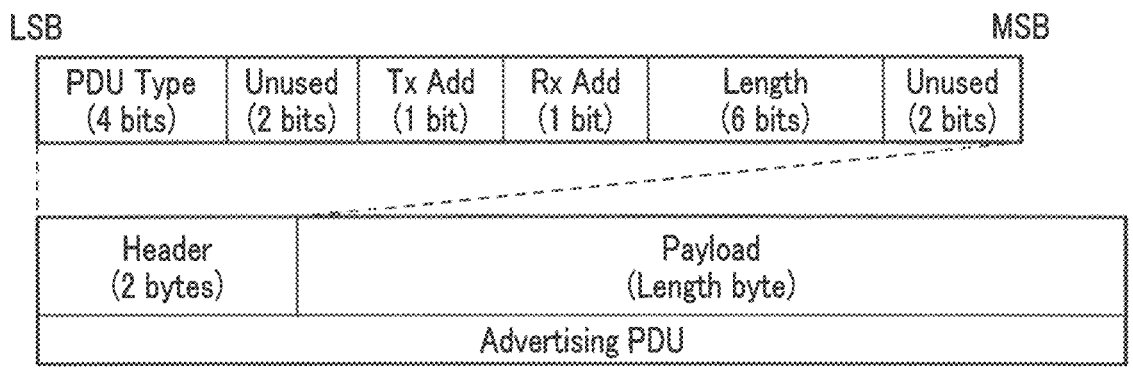
FIG. 8 is a diagram illustrating a data structure of a PDU field of an advertisement packet.

Next, the PDU field of the advertisement packet will be described with reference to FIG. 8. The PDU field of a data communication packet, which is a BLE wireless communication packet transmitted on a data channel, has a data structure different from that shown in FIG. 8. However, the description of such a PDU packet is omitted because the present embodiment does not target a data communication packet.

The PDU field of an advertisement packet includes a 2-byte header and a 0 to 37-byte (variable) payload. The header further includes a 4-bit PDU Type field, a 2-bit unused field, a 1-bit TxAdd field, a 1-bit RxAdd field, a 6-bit Length field, and a 2-bit unused field.

The PDU Type field stores a value indicating a type of this particular PDU. Some values such as "connectable advertising" and "non-connecting advertising" are predefined. The TxAdd field stores a flag indicating whether or not a transmission address is present in the payload. Similarly, the RxAdd field stores a flag indicating whether or not a reception address is present in the payload. The Length field stores a value indicating a byte size of the payload. Given data can be stored in the payload. Accordingly, the measuring device 20 stores a measurement result (SBP and DBP in this example), measurement time information, and a measurement ID in the payload using a predetermined data structure. The payload may further include an identifier representing the measuring device 20 as a transmission source device.

Described in the present embodiment is an example in which all the functions of the measuring device 20 are realized by a general-purpose CPU. However, part or all of the above functions may be realized by one or more dedicated processors.

<Data Management Device>

Figure 9:
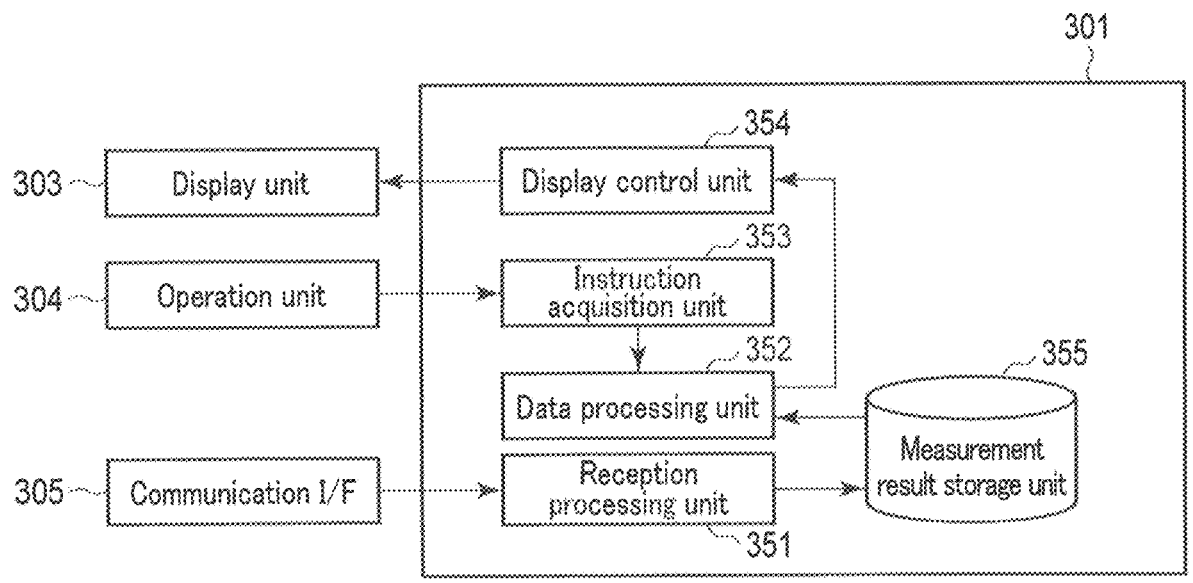
FIG. 9 is a block diagram illustrating an example of a software configuration of the data management device illustrated in FIG. 1.

With reference to FIG. 9, an example of a software configuration of the data management device 30 according to the present embodiment will be described.

The controller 301 of the data management device 30 (FIG. 3) loads into the RAM, a lifestyle management program stored in the storage unit 302. Then, the controller 301 causes the CPU to interpret and execute the lifestyle management program loaded into the RAM, thereby controlling each element. In this manner, as illustrated in FIG. 6, the data management device 30 functions as a computer including a reception processing unit 351, a data processing unit 352, an instruction acquisition unit 353, a display control unit 354, and a measurement result storage unit 355. The measurement result storage unit 355 is realized by the storage unit 302.

The reception processing unit 351 receives a packet from the measuring device 20 via the communication interface 305. The reception processing unit 351 confirms an identifier included in the packet, and discards the received packet when a value of the identifier is inappropriate. When a value of the identifier is appropriate, the reception processing unit 351 extracts a measurement result, measurement time information, and a measurement ID included in the packet, and stores them in the measurement result storage unit 355.

The data processing unit 352 processes measurement results stored in the measurement result storage unit 355. For example, the data processing unit 352 graphs measurement results. Furthermore, the data processing unit 352 determines the presence or absence of data loss, that is, whether or not there is any unreceived measurement result. The data processing unit 352 determines the presence or absence of data loss by, for example, confirming the continuity of measurement IDs. A specific example of the determination method will be described later. The data management device 30 is incapable of informing the measuring device 20 of data loss even if it is detected, because the communication between the measuring device 20 and the data management device 30 is a one-way communication from the measuring device 20 to the data management device 30. For this reason, the data management device 30 presents (for example, displays) the presence of unreceived measurement result to a user. Information to be presented includes a measurement ID of an unreceived measurement result. In this manner, a user is encouraged to input to the measuring device 20 an instruction for transmitting an unreceived measurement result.

The data processing unit 352 may not have a function of determining the presence or absence of data loss. In such a case, a user may discover data loss when he or she is browsing measurement results on the data management device 30.

The instruction acquisition unit 353 acquires an instruction input by a user using the operation unit 204 and passes this instruction to the data processing unit 352. Examples of the instruction include an instruction for displaying a measurement result, etc. The display control unit 354 controls the operation of the display unit 303. For example, the display control unit 354 generates image data including a graph generated by the data processing unit 352 and provides the image data to the display unit 303.

Described in the present embodiment is an example in which all the functions of the data management device 30 are realized by a general-purpose CPU. However, part or all of the above functions may be realized by one or more dedicated processors.

§ 3 Example of Operation

<Measuring Device>

An operation example of the measuring device 20 according to the present embodiment will be described.

Figure 10:
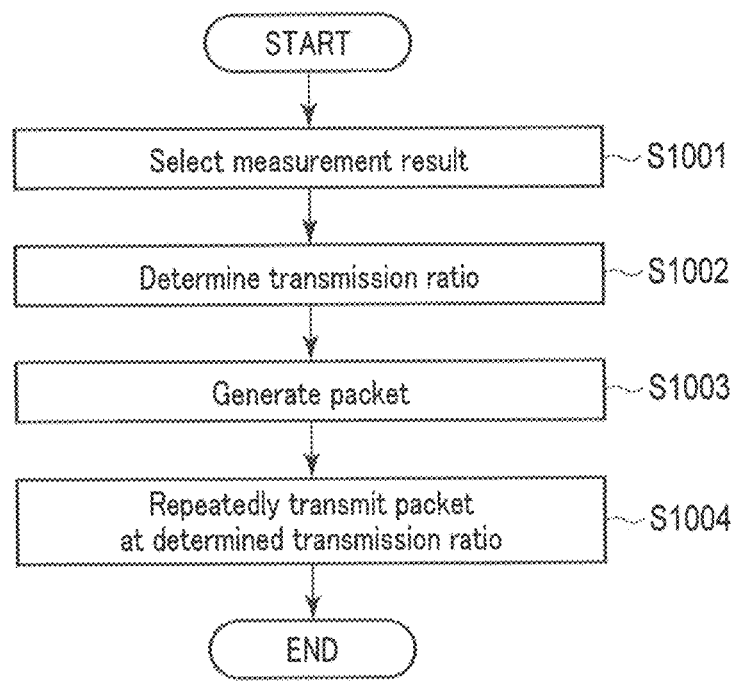
FIG. 10 is a flowchart illustrating an example of a transmission operation in a normal transmission mode according to the present embodiment.

FIG. 10 illustrates an example of a transmission operation in the normal transmission mode of the measuring device 20. The transmission operation illustrated in FIG. 10 starts, for example, when the transmission mode is switched to the normal transmission mode. In step S1001 of FIG. 10, the controller 201 of the measuring device 20 functions as the measurement result selection unit 256 and selects a plurality of measurement results to transmit, from measurement results stored in the storage unit 202 (specifically, the measurement result storage unit 261). For example, the controller 201 selects two measurement results, that is, measurement result 1 and measurement result 2 (the latest measurement result at the present time) obtained after measurement result 1.

In step S1002, the controller 201 functions as the transmission ratio determination unit 257, and determines a transmission ratio for each of the selected measurement results. For example, the controller 201 determines transmission ratios in a manner such that a newer measurement result has a higher transmission ratio. For example, the controller 201 sets the transmission ratio of 2/3 for measurement result 2 and the transmission ratio of 1/3 for measurement result 1. In step S1003, the controller 201 functions as the packet generation unit 258, and generates a plurality of packets based on the selected measurement results. Each packet includes at least one of the selected measurement results. For example, the controller 201 generates packet 1 including measurement result 1 and packet 2 including measurement result 2.

In step S1004, the controller 201 functions as the packet transmission unit 259, and transmits the generated packets according to the determined transmission ratios. The processing shown in step S1004 is continued until, for example, the transmission mode is switched. For example, the controller 201 repeats the operation of transmitting packet 1 once and packet 2 twice.

When measurement result 3 subsequent to measurement result 2 is obtained, the transmission mode is switched to the latest measurement result transmission mode and is then restored to the normal transmission mode, as will be described later. At this time, the controller 201 repeats the operation of transmitting packet 2 including measurement result 2 once and transmitting packet 3 including measurement result 3 twice.

FIG. 11 illustrates an example of a transmission operation in the latest measurement result transmission mode of the measuring device 20. The transmission operation illustrated in FIG. 11 starts when the transmission mode is switched to the latest measurement result transmission mode. In step S1101 of FIG. 11, the controller 201 functions as the measurement result selection unit 256 and selects the latest measurement result from the measurement results stored in the storage unit 202. In step S1102, the controller 201 functions as the packet generation unit 258 and generates a packet including the latest selected measurement result. In step S1103, the controller 201 functions as the packet transmission unit 259 and transmits the generated packet. The processing shown in step S1103 is continued until, for example, the transmission mode is switched.

FIG. 12 illustrates an example of a transmission operation in a designated measurement result transmission mode of the measuring device 20. The transmission operation illustrated in FIG. 12 starts when the transmission mode is switched to the designated measurement result transmission mode. In step S1201 of FIG. 12, the controller 201 functions as the measurement result selection unit 256 and selects a measurement result designated by a user, from measurement results stored in the storage unit 202. In step S1202, the controller 201 functions as the packet generation unit 258 and generates a packet including the selected measurement result. In step S1203, the controller 201 functions as the packet transmission unit 259 and transmits the generated packet. The processing shown in step S1203 is continued until, for example, the transmission mode is switched.

Figure 13:
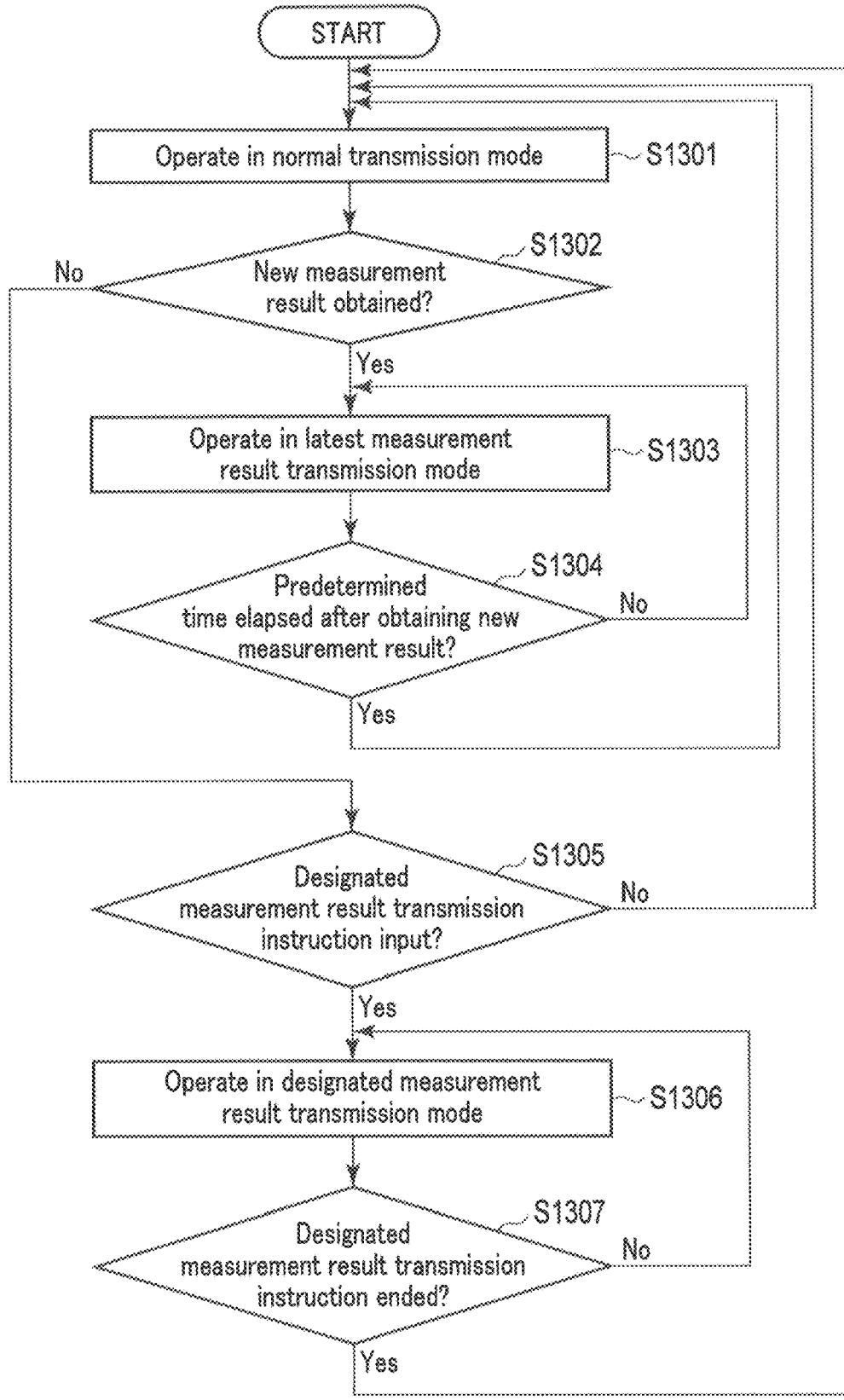
FIG. 13 is a flowchart illustrating an example of a transmission mode switching operation according to the present embodiment.

FIG. 13 illustrates an example of the transmission mode switching operation of the measuring device 20. In step S1301 of FIG. 13, the controller 201 operates in the normal transmission mode. In the normal transmission mode, the controller 201 performs the processing described above with reference to FIG. 10.

In step S1302, the controller 201 determines whether or not a new measurement result is obtained. If no new measurement result is obtained, the processing proceeds to step S1305. If a new measurement result is obtained, the processing proceeds to step S1303.

In step S1303, the transmission mode is switched from the normal transmission mode to the latest measurement result transmission mode. In the latest measurement result transmission mode, the controller 201 performs the processing described above with reference to FIG. 11. In step S1304, the controller 201 determines whether or not a predetermined time (for example, 5 minutes) has elapsed after the obtainment of a new measurement result. Until a predetermined time has elapsed after the obtainment of a new measurement result, the controller 201 operates in the latest measurement result transmission mode. When a predetermined time elapses after the obtainment of a new measurement result, the processing returns to step S1301, and the transmission mode is switched from the latest measurement result transmission mode to the normal transmission mode.

If the processing proceeds from step S1302 to step S1305, the controller 201 determines in step S1305 whether or not a user has input an instruction for transmitting a specific measurement result (designated measurement result transmission instruction). If no designated measurement result transmission instruction is input by a user, the processing returns to step S1301. If a designated measurement result transmission instruction is input by a user, the processing proceeds to step S1306. The designated measurement result transmission instruction corresponds to the fact that a user operates the operation unit 204 so as to cause the display unit 203 to display a specific measurement result.

In step S1306, the transmission mode is switched from the normal transmission mode to the designated measurement result transmission mode. In the designated measurement result transmission mode, the controller 201 performs the processing described above with reference to FIG. 12.

In step S1307, the controller 201 determines whether or not the designated measurement result transmission instruction has ended. For example, when a user inputs an instruction to switch from a screen for confirming a history of measurement results to a home screen, the controller 201 determines that the designated measurement result transmission instruction has ended. Until the designated measurement result transmission instruction ends, the controller 201 operates in the designated measurement result transmission mode. If the designated measurement result transmission instruction ends, the processing returns to step S1301 and the transmission mode is switched from the designated measurement result transmission mode to the normal transmission mode.

The processing procedure described above is merely an example, and each processing may be changed to the extent possible. Furthermore, in the processing procedure described above, steps can be omitted, replaced, and added as appropriate according to the embodiment. For example, the processing in step S1003 may be executed after the processing in step S1002, or may be executed in parallel with the processing in step S1002. In the transmission mode switching operation, the controller 201 operating even in the latest measurement result transmission mode may determine whether or not a user has input a designated measurement result transmission instruction. If a user inputs the designated measurement result transmission instruction while the controller 201 is operating in the latest measurement result transmission mode, the transmission mode is switched from the latest measurement result transmission mode to the designated measurement result transmission mode.

Described in the present embodiment is an example in which all the functions of the measuring device 20 are realized by a general-purpose CPU. However, part or all of the above functions may be realized by one or more dedicated processors.

<Data Management Device>

An operation example of the data management device 30 according to the present embodiment will be described.

Figure 14:
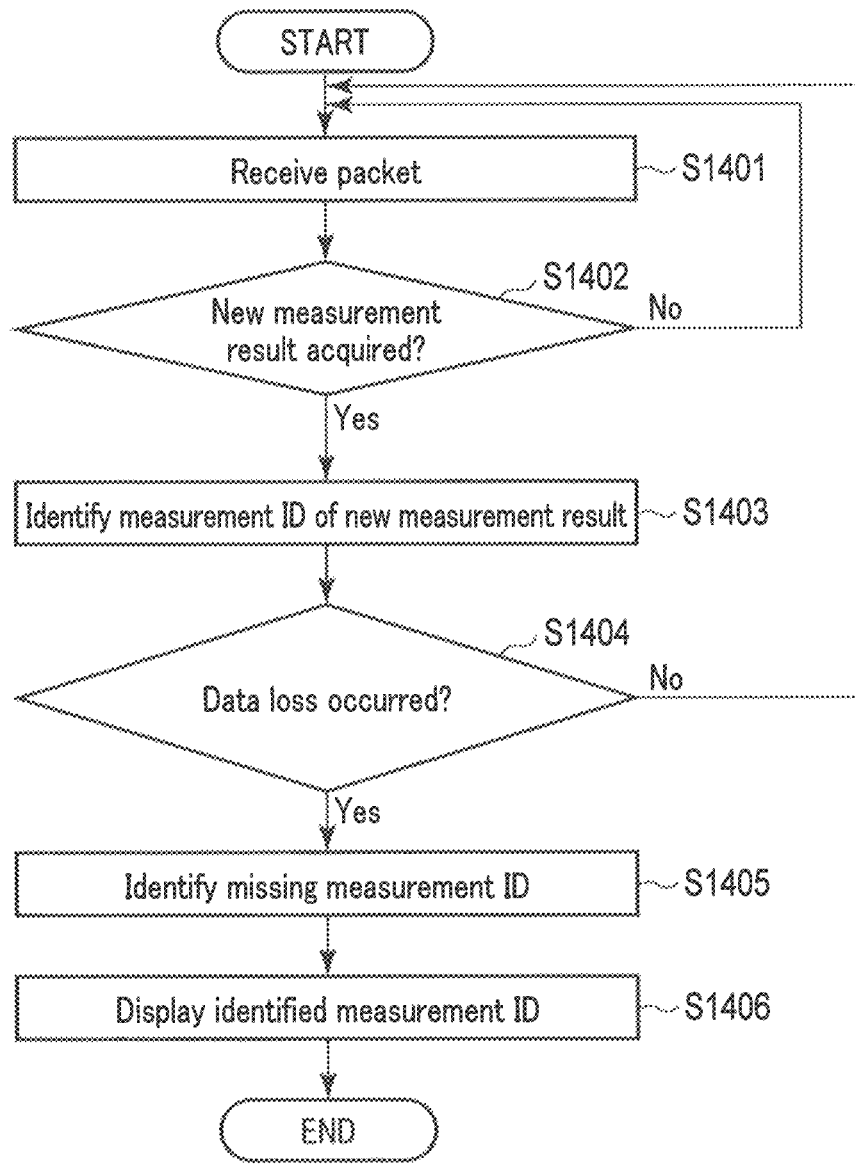
FIG. 14 is a flowchart illustrating an example of a data management operation according to the present embodiment.

FIG. 14 illustrates an example of a processing procedure of the data management device 30. This example assumes that the measuring device 20 is designed to transmit 10 measurement results in order from the latest.

In step S1401 shown in FIG. 14, the controller 301 of the data management device 30 functions as a reception processing unit 351, receives a packet from the measuring device 20 via the communication interface 305, and obtains a measurement result included in the received packet. In step S1402, the controller 301 functions as the data processing unit 352, and determines whether or not the obtained measurement result is a new measurement result (a measurement result that has not been received so far). If the obtained measurement result is not new, the processing returns to step S1401, and the controller 301 receives a next packet. If a new measurement result is received from the measuring device 20, the processing proceeds to step S1403. In step S1403, the controller 301 functions as the data processing unit 352 and identifies an ID of the received new measurement result.

In step S1404, the controller 301 functions as the data processing unit 352, and makes a determination with respect to a set of IDs that are smaller than the identified ID by 10 or more, whether or not data loss has occurred. If the measuring device 20 transmits 10 newer measurement results, any measurement result with an ID that is smaller than the identified ID by 10 or more is not transmitted in the normal transmission mode. In other words, the data management device 30 misses the chance to receive a measurement result with an ID that is smaller than the identified ID by 10 or more. For this reason, in order to solve the data loss, a user needs to instruct the measuring device 20 to transmit a measurement result that has not been received by the data management device 30. If data loss has occurred, the processing proceeds to step S1405. If no data loss has occurred, the processing returns to step S1401. As an example, in the case of a new measurement result being assigned with ID of 257, the controller 301 determines whether or not all the measurement results assigned with IDs 1 to 247 are present in the measurement result storage unit 355. If all the measurement results with IDs 1 to 247 are present, the controller 301 determines that no data loss has occurred. If not, the controller 301 determines that data loss has occurred.

In step S1405, the controller 301 functions as the data processing unit 352 and identifies a missing ID. In step S1406, the controller 301 functions as the display control unit 354 and causes the display unit 303 to display information indicating the identified ID. In the above example, for example, if the measurement result with ID=247 is absent in the measurement result storage unit 355, the display unit 303 displays the message that "measurement result with ID 247 has not been received". A user confirms the information displayed on the display unit 303 and inputs to the measuring device 20, an instruction for transmitting a measurement result that has not been received by the data management device 30.

In this way, the data management device 30 presents to a user, information indicating an unreceived measurement result. This encourages a user to input to the measuring device 20, an instruction for causing the measuring device 20 to transmit a measurement result that has not been received by the data management device 30. In response to a user's operation, the measuring device 20 transmits a measurement result that has not been received by the data management device 30, and the data management device 30 receives this measurement result. As a result, data loss can be solved in the data management device 30.

Described in the present embodiment is an example in which all the functions of the data management device 30 are realized by a general-purpose CPU. However, part or all of the above functions may be realized by one or more dedicated processors.

(Advantageous Effect)

As described above, the measuring device 20 according to the present embodiment transmits each one of measurement results in a one-way communication packet during not only a period from when this particular one measurement result is obtained until a next measurement result is obtained, but also a period after the next measurement result is obtained. This increases the possibility that each measurement result is successfully received by the data management device 30. As a result, the occurrence of data loss in the data management device 30 can be reduced.

The measuring device 20 determines a transmission ratio for each of measurement results to transmit. For example, the measuring device 20 sets a transmission ratio for the first measurement result to a value larger than that of a transmission ratio of the second measurement result generated before the first measurement result. The possibility that first measurement result which is a newer measurement result has been received by the data management device 30 is low. The possibility that the second measurement result which is an older measurement result has been received by the data management device 30 is high. A measurement result with a low possibility of being successfully received by the data management device 30 is transmitted at high density (i.e., densely), and a measurement result with a high possibility of being successfully received by the data management device 30 is transmitted at low density (i.e., sparsely). In this manner, the occurrence of data loss in the data management device 30 can be reduced, and the reception of a new measurement result by the data management device 30 is facilitated.

In the present embodiment, measurement results are transmitted by one-way communication. This frees a user from complicated pre-setting such as pairing in Bluetooth. As a result, usability can be improved. Furthermore, this case does not require each of the measuring device 20 and the data management device 30 to execute a complicated communication procedure. Thus, this case has advantages over the case of using two-way communication, in that hardware resources such as a processor and a memory can be saved and development and/or evaluation costs can be reduced.

§ 4 Modification

In the present embodiment described above, the measuring device 20 measures blood pressure using the oscillometric method. The measuring device 20 may measure the blood pressure by other methods. The measuring device 20 may be a blood pressure measuring apparatus configured to obtain a blood pressure value for each heartbeat. For example, the measuring device 20 may measure blood pressure by the tonometry method. The measuring device 20 may detect a pulse transit time (PTT), which is a propagation time of a pulse wave propagating through an artery, using two or more electrodes, and estimate a blood pressure value (for example, SBP and DBP) based on the detected pulse propagation time. The measuring device 20 may measure a volume pulse wave optically and estimate a blood pressure value based on the measurement result. Furthermore, the measuring device 20 may measure blood pressure using ultrasonic waves.

The measuring device 20 may be a stationary device. For example, the measuring device 20 is used for an unspecified number of patients in a hospital, and the data management device 30 is used to collect measurement results of these patients.

In this embodiment described above, a transmission ratio is assigned to each of a plurality of measurement results to be transmitted. A transmission ratio may be set to the same value for all of the measurement results to be transmitted. In this case, the transmission processing unit 255 may not include the transmission ratio determination unit 257.

Data stored in a payload of a packet may be encrypted. As an example, the measuring device 20 causes the display unit 203 to display an encryption key used for encryption, and a user confirms the encryption key and inputs it to the data management device 30 using the operation unit 304. The controller 301 of the data management device 30 decrypts the payload portion of the packet using this encryption key. This enables the transmission of a measurement result from the measuring device 20 to the data management device 30 without concern for data leakage. An encryption key may be changed periodically.

A quantity (e.g., a physical quantity) to be measured is not limited to a quantity related to user information. For example, a quantity to be measured may be a quantity related to the environment such as temperature or radiation dose.

In short, the present invention is not limited to the above-described embodiments and can be embodied in practice by modifying the elements without departing from the gist of the invention. In addition, various inventions can be made by suitably combining the elements disclosed in connection with the above embodiments. For example, some of the entire elements described in the embodiments may be omitted. In addition, the elements between different embodiments may be combined as appropriate.

§ 5 Additional Note

Part or all of the above-mentioned embodiments may also be described as in the following additional notes, without limitation thereto.

(Additional Note 1)

A measuring device comprising:

at least one processor; and a memory connected to the at least one processor;

wherein the at least one processor is configured to:

acquire, from a sensor, a plurality of measurement results obtained by measuring a quantity related to information at time intervals using the sensor, the plurality of measurement results including a first measurement result, a second measurement result obtained after the first measurement result, a third measurement result obtained after the second measurement result, and a fourth measurement result obtained after the third measurement result;

transmit a plurality of measurement results including the first measurement result and the second measurement result, in a one-way communication packet during a first period from acquisition of the second measurement result to acquisition of the third measurement result; and transmit a plurality of measurement results including the second measurement result and the third measurement result, in the one-way communication packet during a second period from when the third measurement result is obtained until the fourth measurement result is obtained.

(Additional Note 2)

A transmission method to be performed by a measuring device, the method comprising:

acquiring by using at least one processor, from a sensor, a plurality of measurement results obtained by measuring a quantity related to information at time intervals using the sensor, the plurality of measurement results including a first measurement result, a second measurement result obtained after the first measurement result, a third measurement result obtained after the second measurement result, and a fourth measurement result obtained after the third measurement result;

transmitting by using at least one processor, a plurality of measurement results including the first measurement result and the second measurement result, in a one-way communication packet during a first period from when the second measurement result is obtained until the third measurement result is obtained; and transmitting by using at least one processor, a plurality of measurement results including the second measurement result and the third measurement result, in the one-way communication packet during a second period from when the third measurement result is obtained until the fourth measurement result is obtained.

REFERENCE SIGNS LIST

10 . . . Data management system
20 . . . Measuring device
21 . . . Sensor
22 . . . Measurement control unit
23 . . . Measurement result acquisition unit
24 . . . Transmission processing unit
25 . . . Transmitter
26 . . . Measurement result storage unit
201 . . . controller
202 . . . storage unit
203 . . . Display unit
204 . . . Operation unit
205 . . . Communication interface
206 . . . Battery
207 . . . Blood pressure measuring unit
208 . . . Cuff
209 . . . Pump
210 . . . Exhaust valve
211 . . . Pressure sensor
212 . . . Air passage
251 . . . Measurement control unit
252 . . . Air supply control unit
253 . . . Blood pressure value calculation unit
254 . . . Instruction acquisition unit
255 . . . Transmission processing unit
256 . . . Measurement result selection unit
257 . . . Transmission ratio determination unit
258 . . . Packet generation unit
259 . . . Packet transmission unit
260 . . . Display control unit
261 . . . Measurement result storage unit
30 . . . Data management device
31 . . . Receiver
32 . . . Reception processing unit
33 . . . Data processing unit
34 . . . Measurement result storage unit
301 . . . Controller
302 . . . Storage unit
303 . . . Display unit
304 . . . Operation unit
305 . . . Communication interface
306 . . . Battery
351 . . . Reception processing unit
352 . . . Data processing unit
353 . . . Instruction acquisition unit
354 . . . Display control unit
355 . . . Measurement result storage unit

The invention claimed is:

1. A measuring device comprising:
at least one processor; and
a memory connected to the at least one processor;
wherein the at least one processor is configured to:
acquire, from a sensor, a plurality of measurement results obtained by measuring a value related to information at time intervals using the sensor, the plurality of measurement results including a first measurement result, a second measurement result obtained after the first measurement result, a third measurement result obtained after the second measurement result, and a fourth measurement result obtained after the third measurement result;

transmit a plurality of measurement results including the first measurement result and the second measurement result, in a one-way communication packet during a first period from when the second measurement result is obtained until the third measurement result is obtained;

transmit a plurality of measurement results including the second measurement result and the third measurement result, in the one-way communication packet during a second period from when the third measurement result is obtained until the fourth measurement result is obtained;

determine a transmission ratio indicating a number of packets used to transmit each measurement result with respect to a number of packets transmitted in one cycle; and set during the second period, a transmission ratio for the second measurement result to a value smaller than a value of a transmission ratio for the third measurement result.

2. The measuring device according to claim 1, wherein the at least one processor is further configured to:

acquire from a user, an instruction for designating a fifth measurement result selected by the user from the acquired measurement results;

display the fifth measurement result on a display unit; and transmit only the fifth measurement result in the one-way communication packet during a third period in which the fifth measurement result is displayed on the display unit.

3. The measuring device according to claim 1, wherein the at least one processor is further configured to transmit only the second measurement result in the one-way communication packet until a predetermined time elapses after the second measurement result is obtained.

4. The measuring device according to claim 1, wherein the information includes at least one of user's biological information and user's activity information.

5. A transmission method to be performed by a measuring device, the transmission method comprising:

acquiring, from a sensor, a plurality of measurement results obtained by measuring a value related to information at time intervals using the sensor, the plurality of measurement results including a first measurement result, a second measurement result obtained after the first measurement result, a third measurement result obtained after the second measurement result, and a fourth measurement result obtained after the third measurement result;

transmitting a plurality of measurement results including the first measurement result and the second measurement result, in a one-way communication packet during a first period from when the second measurement result is obtained until the third measurement result is obtained;

transmitting a plurality of measurement results including the second measurement result and the third measurement result, in the one-way communication packet during a second period from when the third measurement result is obtained until the fourth measurement result is obtained;

determining a transmission ratio indicating a number of packets used to transmit each measurement result with respect to a number of packets transmitted in one cycle; and setting during the second period, a transmission ratio for the second measurement result to a value smaller than a value of a transmission ratio for the third measurement result.

6. A non-transitory computer readable medium including computer executable instructions, wherein the instructions, when executed by a processor, cause the processor to perform a method comprising:

acquiring, from a sensor, a plurality of measurement results obtained by measuring a value related to information at time intervals using the sensor, the plurality of measurement results including a first measurement result, a second measurement result obtained after the first measurement result, a third measurement result obtained after the second measurement result, and a fourth measurement result obtained after the third measurement result;

transmitting a plurality of measurement results including the first measurement result and the second measurement result, in a one-way communication packet during a first period from when the second measurement result is obtained until the third measurement result is obtained;

transmitting a plurality of measurement results including the second measurement result and the third measurement result, in the one-way communication packet during a second period from when the third measurement result is obtained until the fourth measurement result is obtained;

determining a transmission ratio indicating a number of packets used to transmit each measurement result with respect to a number of packets transmitted in one cycle; and setting during the second period, a transmission ratio for the second measurement result to a value smaller than a value of a transmission ratio for the third measurement result.

* * * * *